United States Patent [19]

Hatano

[11] Patent Number: 5,228,429
[45] Date of Patent: Jul. 20, 1993

[54] POSITION MEASURING DEVICE FOR ENDOSCOPE

[76] Inventor: Tadashi Hatano, 2-96-1, Syuri-ishimine, Naha-shi, Okinawa-ken, Japan

[21] Appl. No.: 983,245

[22] Filed: Nov. 30, 1992

Related U.S. Application Data

[62] Division of Ser. No. 820,253, Jan. 14, 1992, abandoned.

[30] Foreign Application Priority Data

Jan. 14, 1991 [JP] Japan .................. 2-004431

[51] Int. Cl.⁵ .................................................. A61B 1/04
[52] U.S. Cl. .......................................... 128/4; 606/53; 606/108; 901/9
[58] Field of Search ............... 604/116; 606/53–108, 606/19, 45, 46; 128/4, 6; 433/27, 54, 55, 72; 312/209; 901/9

[56] References Cited

U.S. PATENT DOCUMENTS

| | | | |
|---|---|---|---|
| 3,994,557 | 11/1976 | Hopkins | 128/4 X |
| 4,235,437 | 11/1980 | Ruis et al. | 482/113 X |
| 4,545,713 | 10/1985 | Beni et al. | 606/19 X |
| 4,660,560 | 4/1987 | Klein | 606/108 |
| 4,854,301 | 8/1989 | Nakajima | 128/4 |
| 4,907,395 | 3/1990 | Opie et al. | 128/4 X |
| 4,979,949 | 12/1990 | Matsen, III et al. | 606/53 |
| 5,049,028 | 9/1991 | Asano et al. | 901/9 X |
| 5,054,491 | 10/1991 | Saito et al. | 128/4 X |
| 5,078,743 | 1/1992 | Mikalov et al. | 606/108 X |
| 5,086,401 | 2/1992 | Glassman et al. | 606/53 X |

OTHER PUBLICATIONS

Elmed Endoscopic Fixation Device brochure.

Primary Examiner—V. Millin
Assistant Examiner—J. Doyle
Attorney, Agent, or Firm—Sherman and Shalloway

[57] ABSTRACT

A plurality of arms are successively connected to a fixed arm so that the free end of the connected arms is movable three-dimensionally, a direct-access endoscope is attached to the three-dimensionally movable free end of the arms, and angle sensors are provided in the individual arm joints. Changes in angles between the individual arms due to the movement of the front end of the direct-access endoscope are sensed by the angle sensors, and the size and position of the object are numerically determined according to the changes.

1 Claim, 1 Drawing Sheet

POSITION MEASURING DEVICE FOR ENDOSCOPE

This application is a division of application Ser. No. 07/820,253, filed Jan. 14, 1992, now abandoned.

FIELD OF THE INVENTION

This invention relates to a device for use with an endoscope used in medical applications and the like for measuring size and position of an object observed using the endoscope.

DESCRIPTION OF PRIOR ART

Heretofore, various types of endoscopes have been used for observing spaces in the human body, that is, the inner surface of hollow organs and the inside of the cavity and abdominal cavity. The endoscope plays an important role in diagnosis since it enables visual observation of the inside of the body from outside.

However, endoscopes, although having advantages of enabling direct visual identification of the presence and shape of an object within the body such as tumors, have had inconveniences in that they cannot numerically measure the size and position of the observed object. For example, the size of a tumor observed by the endoscope is largely affected by the distance between the tumor and the endoscope, and detailed and objective data cannot be obtained.

It is a primary object of the present to provide a device for observing an object using an endoscope and numerically measuring the size and position of the object.

SUMMARY OF THE INVENTION

In accordance with the present invention, there is provided a position measuring device for an endoscope comprising a plurality of arms successively connected to a fixed arm so that a free end of the connected plurality of arms is movable three-dimensionally, a direct-access endoscope connected to the free end of the connected arms, and angle sensors provided in individual arm joints.

To make the free end of the arms after connection movable three-dimensionally, the plurality of arms are successively connected to the fixed arm using at least one joint which is rotatable in the horizontal direction relative to the vertical axis of the arm and at least one joint which is rotatable in the vertical axis direction.

Alternatively, to make the free end of the arms movable three-dimensionally, for example, two rails are individually provided with sliders, the sliders are connected by two rails, a base plate is slidably mounted to the rails connecting the sliders, and a vertically expandable, rotatable arm may be mounted under the base plate.

DESCRIPTION OF THE PREFERRED EMBODIMENT

Figure 1:
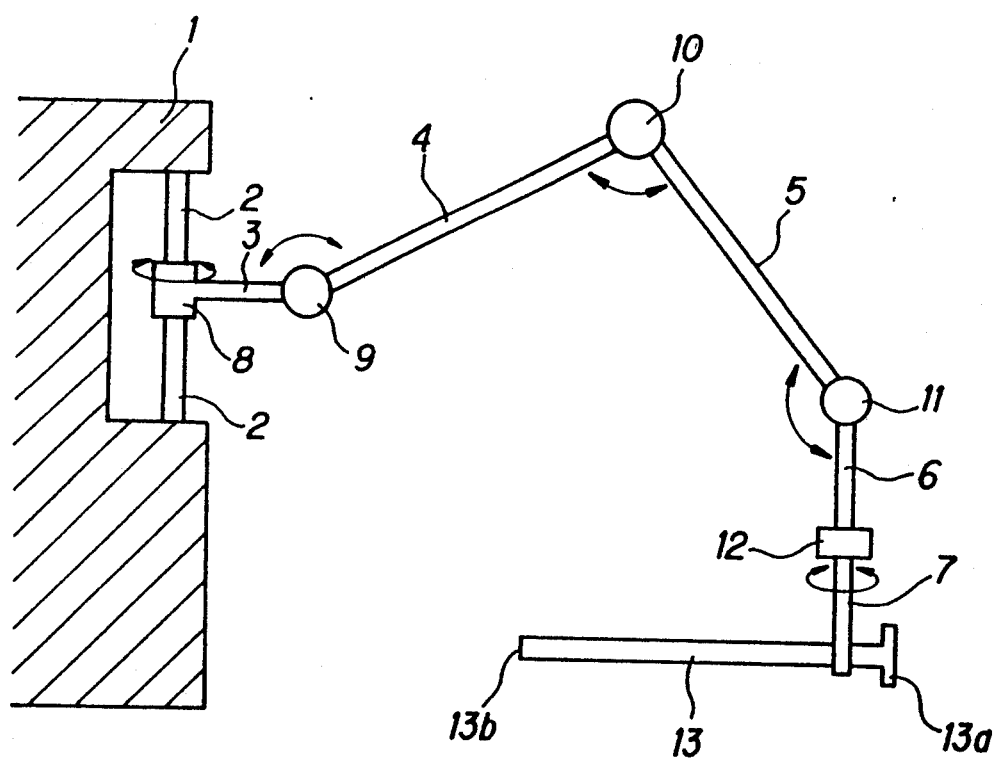
FIG. 1 is a schematic view of the position measuring device for an endoscope according to the present invention.

The present invention will now be described in detail with reference to FIG. 1 showing an embodiment. In FIG. 1, numeral 1 indicates a fixture, numeral 2 indicates a fixed arm, numerals 3, 4, 5, 6, and 7 indicate arms, numerals 8, 9, 10, 11, and 12 indicate angle sensors provided at individual arm joints, numeral 13 indicates a direct-access endoscope, numeral 13a indicates an ocular, and numeral 13b indicates a front end.

The fixed arm 2 is mounted to the fixture 1. One end of the arm 3 is connected to the fixed arm 2 so that the arm 3 is rotatable in the horizontal direction relative to the vertical axis of the fixed arm 2. The other end of the arm 3 is connected to one end of the arm 4 so that the arm 4 is rotatable in the vertical axis direction of the arm 3. The other end of the arm 4 is connected to one end of the arm 5 so that the arm 5 is rotatable in the vertical axis direction of the arm 4. The other end of the arm 5 is connected to one end of the arm 6 so that the arm 5 is rotatable in the vertical direction of the arm 5. Furthermore, the other end of the arm 6 is connected to one end of the arm 7 so that the arm 7 is rotatable in the horizontal direction relative to the vertical axis of the arm 6. The rotatable connection is achieved using conventional means known in the art. The direct-access endoscope 13 is vertically attached to the other end of the arm 7, and the angle sensors 8, 9, 10, 11, and 12, which are of a conventional type known in the art, are attached to the individual joints.

Since the individual joints between the fixed arm and the arm 3 and between the arm 6 and the arm 7 are rotatable in the horizontal directions relative to the vertical axes of the individual arms, and the individual joints between the arm 3 and the arm 4, between the arm 4 and the arm 5, and between the arm 5 and the arm 6 are rotatable in the vertical axis directions of the individual arms, the direct-access endoscope attached to the free end of the arm 7 is movable in all directions, that is, three-dimensionally. The movement, that is, changes in angle between the individual arms, is sensed and recorded by the individual angle sensors provided in the individual joints. The record is preferably inputted to a computer.

This example uses 5 arms, and 5 joints and angle sensors. It is preferable to use 5 or more arms and 5 each or more joints and angle sensors in order to achieve free movement of the direct-access endoscope in all directions. However, the relative positions between a joint rotatable in the horizontal direction relative to the vertical axis of an arm and a joint rotatable in the vertical axis direction of an arm are not specifically limited.

A measurement method using the inventive measuring device will now be described. Viewing from the ocular 13a of the direct-access endoscope, position of the front end 13b of the direct-access endoscope is aligned with an object to be measured, for example, one end of a tumor. Individual angles between the fixed arm 2 and the arm 3, the arm 3 and the arm 4, the arm 4 and the arm 5, the arm 5 and the arm 6, and the arm 6 and the arm 7 are sensed by the angle sensors, and inputted to the computer to record a three-dimensional position (three-dimensional coordinates) of the front end 13b of the direct-access endoscope. A projection can be attached to the tip of the direct-access endoscope, which is brought in contact with the object to be measured, to achieve simple and precision measurement.

Then, the front end 13b of the direct-access endoscope is moved to be aligned with the other end of the tumor. As the front end 13b moves, the individual arms move and angles between the individual arms are changed. The angles after movement are sensed by the angle sensors and inputted to the computer to record a three-dimensional position (three-dimensional coordinates) of the front end 13b of the direct-access endoscope after the movement. The lengths of the individual arms and the length of the direct-access endoscope are previously measured and inputted to the computer. The three-dimensional position (three-dimensional coordinates) of the front end of the direct-access endoscope can be determined from the previously-stored values and the angles between the individual arms. Then, an actual length from one end to the other of the tumor is calculated, using a conventional method known in the art, from the two three-dimensional positions (three-dimensional coordinates) of the front end 13b of the direct-access endoscope before and after the movement.

This method can measure not only the size of the tumor but also its area and distance from a specific portion. The endoscope used in the present invention is of a direct-access type which uses a lens to observe an object from outside of the body, but a fiber scope used for observation of digestive canals is not suitable for the purpose.

With the position measuring device for an endoscope according to the present invention, for example, a tumor in the human body can be observed for its shape and measured for its size, position, area and the like, and the results are obtained as numerical values.

What is claimed is:

1. A method for measuring the size and/or position of an object within a body cavity, comprising (A) providing a fixed arm;
(B) providing a plurality of movable arms successively connected to one another through respective arm joints, each of said movable arms having a predetermined length, said plurality of successively connected arms having a fixation end and a free end, said fixation end connected to said fixed arm through a joint, said arm joints and said joint each comprising a pivot permitting relative rotation of the arms connected thereto about an axis, each said axis of each said pivot being either a vertical axis or a horizontal axis, at least one of said arm joints and said joint being a pivot permitting relative rotation about a vertical axis, at least one of said arm joints and said joint being a pivot permitting relative rotation about a horizontal axis;
(C) fixedly connecting a direct-access endoscope, having a front end, to said free end of said plurality of successively connected arms with said front end of said endoscope at a predetermined distance from said free end of said plurality of successively connected arms;
(D) providing a plurality of angle measuring devices, each angle measuring device operatively associated with a respective one of said arm joints and said joint, for measuring the angle of relative rotation at each of said arm joints and said joint;
(E) inserting the front end of said endoscope into a body cavity of a patient;
(F) bringing the front end of said endoscope into contact with a portion of an object within said body cavity;
(G) calculating a three dimensional coordinate position of said front end, relative to said fixed arm, utilizing said predetermined distance of said front end from said free end, said predetermined lengths of said successively connected arms and said angles of relative rotation at each of said arm joints and said joint;
(H) bringing the front end of said endoscope into contact with a different portion of said object within said body cavity;
(I) calculating a three dimensional coordinate position of said front end, relative to said fixed arm, utilizing said predetermined distance of said front end from said free end, said predetermined lengths of said successively connected arms and said angles of relative rotation at each of said arm joints and said joint;
(J) repeating steps (H) and (I) to establish the size and position of said object within said body cavity.

* * * * *